US006555347B1

(12) United States Patent
Rome et al.

(10) Patent No.: US 6,555,347 B1
(45) Date of Patent: Apr. 29, 2003

(54) HUMAN MINOR VAULT PROTEIN P193

(75) Inventors: Leonard H. Rome, Tarzana, CA (US); Valerie A. Kickhoefer, Sherman Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/607,510

(22) Filed: Jun. 28, 2000

Related U.S. Application Data

(63) Continuation of application No. 09/089,621, filed on Jun. 3, 1998, now Pat. No. 6,156,879.

(51) Int. Cl.[7] .......................... C12P 21/02; C12N 15/85; C12N 15/86; C12N 15/11; C07H 21/04
(52) U.S. Cl. .................... 435/71.1; 435/69.1; 435/69.3; 435/70.1; 435/325; 435/320.1; 536/23.5; 536/23.1; 536/25.1
(58) Field of Search .............................. 536/23.5, 23.1, 536/25.1; 435/325, 320.1, 69.1, 70.1, 70.3, 71.1, 71.2, 69.3

(56) References Cited

PUBLICATIONS

Kickhoefer, V.A. et al. The 193–kD vault porotein, VPARP, is a novel poly(ADP–ribose) polymerase. J. Cell Biology, 146(5): 917–928, 1999.*
Accession No. N78296, Database GenBank EST, Hillier, L. et al. Genome Res. 6(9): 807–828, 1996.*
Accession No. AA034060, Database GenBank EST, Hillier, L. et al., Genome Res. 6(9): 807–828, 1996.*
Accession No. AA622038, Database GenBank EST, NCI–CGAP, Oct. 14, 1997.*
Accession No. AA52384, Database GenBank EST, NCI–CGAP, Aug. 5, 1997.*
Sambrook, J. et al. Molecular Cloning, A Laboratory Manual, 2nd Edition, Cold Spring Harbour Laboratory Press, 1989, pp. 16.3, 16.4, 16.17–16.22, 16.28, 16.29, and 17–38–17.41.*
Bork, Peer et al., "A superfamily of conserved domains in DNA damage–responsive cell cycle checkpoint proteins," *The Faseb Journal*, 11:68–76, 1997.
Callebaut, Isabelle et al., "From BRCA1 to RAP1: a widespread BRCT module closely associated with DNA repair," *FEBS Letters*, 400:25–30, 1997.
Database GenBank, Accession No. D79999, Nomura, N., Human mRNA for K1AA0177 gene, partial cds. DDBJ/EMBL/, see entire file.
Golemis, Erica A. et al., "Interaction Trap/Two–Hybrid System to Identify Interacting Proteins," *Current Protocols in Mol. Biol.*, 20.1.1–20.35, John Wiley & Sons, 1997.
Hart, S.M. et al., "Expression of the human major vault protein LRP in acute myeloid leukemia," *Experimental Hematology*, 25(12):1227–1232, Nov. 1997.

Inman, E.M. et al., "Targeted Degradation of the Vault RNA (vRNA) in vivo Using Antisense Oligodeoxynucleotides," *Molecular Biology of the Cell*, vol. 6, Suppl., p. 196a.
Izquierdo, M.A. et al., "Relationship of LRP–human major vault protein to in vitro and clinical resisttance to anticancer drugs," *Cytotechnology*, 19(3):191–197, 1996.
Kedersha, Nancy L. et al., "Vaults.III.Vault Ribonucleoprotein Particles Open into Flower–like Structures with Octagonal Symmetry," *The Journal of Cell Biology*, 112(2):225–235 (1991).
Kickhoefer, V. et al., "Multidrug resistant cancer cell lines contain elevated levels of vaults," *Proc. Amer. Assoc. Cancer Res.*, Mar. 1997, p. 252, Abstract #1694.
Kickhoefer, V.A. et al., "Vault Ribonucleoprotein Particles from Rat and Bullfrog Contain a Related Small RNA That Is Transcribed by RNA Polymerase III," *The Journal of Biological Chemistry*, 268(11):7868–7873, Apr. 15, 1993.
Kickhoefer, Valerie A. et al., "Vaults are the answer, what is the question?" *Trends in Cell Biology*, 6:174–178 1996.
Kickhoefer, V. et al., "Vaults Are Up–regulated in Multidrug–resistant Cancer Cell Lines," *J. Biol. Chem.*, Apr. 10, 1998, vol. 273(15):8971–8974.
Kim, K. et al., "Tumor Suppressor Gene Expression during Normal and Pathologic Myocardial Growth," *J. Biol. Chem.*, 269(36):22607–22613, Sep. 9, 1994.
Nagase, Takahiro et al., "Prediction of the Coding Sequences of Unidentified Human Genes," *DNA Research*, 3:17–24 1996.
Ruf, Armin et al., "Structure of the catalytic fragment of poly(ADP–ribose) polymerase from chicken," *Proc. Natl. Acad. Sci. USA* 93:7481–7485 1996.
Scheffer, George L. et al., "The drug resistance–related protein LRP is the human major vault protein," *Natire Medicine*, 1(6):578–582 1995.
Sebolt–Leopold, Jr. et al., "Enhancement of Alkylating Agent Activity in vitro by PD 128763, a Potent Poly(ADP–ribose) Synthetase Inhibitor," *Int. J. Radiation Oncology Biol. Phys.*, 222:619–621 1992.
Simonin, Frederic et al., "The Carboxyl–terminal Domain of Human Poly(ADP–ribose) Polymerase," *The Journal of Biological Chemistry*, 268(18):13454–13461 1993.

(List continued on next page.)

Primary Examiner—Anthony C. Caputa
Assistant Examiner—Anne L. Holleran
(74) Attorney, Agent, or Firm—David A. Farah; Sheldon & Mak

(57) ABSTRACT

A polynucleotide molecule encoding human minor vault protein p193, or its complementary strands. A purified and isolated polynucleotide molecule consisting essentially of a nucleotide sequence encoding human minor vault protein p193, or its complementary strands, or a combination of a nucleotide sequence encoding human minor vault protein p193 and its complementary strands.

15 Claims, 10 Drawing Sheets

OTHER PUBLICATIONS

Kedersha, N.L. et al, "Vaults. II. Ribonucleoprotein Structures Are Highly Conserved Among Higher and Lower Eukaryotes," *J. Cell Biol.*, 110:895–901 (Apr. 1990).

Kickhoefer, Valerie A. et al., "The 193–kD Vault Protein, VPARP, Is a Novel Poly(ADP–ribose) Polymerase," *J. Cell Biol.*, 146(5):917–928 (Sep. 6, 1999).

Rome, L. et al., "Unlocking vaults: organelles in search of a function," *Trends in Cell Biol.*, 1:47–50 (Aug./Sep. 1991).

Schroeijers, Anouk B. et al., "The Mr 193,000 Vault Protein Is Up–Regulated in Multidrug–resistant Cancer Cell Lines," *Cancer Research*, 60(4):1104–1110 (Feb. 15, 2000).

Silva, A. et al., "Identification and Characterization of the Minor Vault Protein p193," *Mol. Biol. Cell*, 9:69A (Nov. 9, 1998).

* cited by examiner

FIG. 1a

```
CGCCCGCCCCAGCCCCGGGGGCCAGGGCAAAAGCCTAAATTACGCGGAGCAAGGAGCCGGAATCGGGAGCGTCCCGGAGCTAGCTGGATCCTCTA
GCGGGCGGGTCGGGCCCCCGTCCCCGGTTCCCTTCGGATTTAATGCCTTAATGGCTCGTTCCTCGGCCTTCGCGCCTAGCCTGCTAGAACCTAGAGAT      100

GGCAGGATGGTGATGGAATCTTTTGCAAATTGTATCTTTCTGTTTGAAAGTGAAGTACTTACCTCAGCAGCAGAAGAAAAAGCTACAAACTGACATTAAGG
CCGTCCTACCACTACCCTTAGAAACGTTTAACATAGAAGACAAACTTTCACTTCATGAATGGAGTCGTCGTCTTCTTTTTTCGATGTTTGACTGTAATTCC      200

AAAATGGCGGAAAGTTTTCCTTTTCGGTTAAATCCCTCAGTGCACACATATAATCTTAGATAATAATGCTGATGTTCTGAGTCAGTACCAACTGAATTCTATCCA
TTTTACCGCCTTTCAAAAGGAAAAGCCAATTTAGGAGTCACGTGTGTATATTAGAATCTATTACGACTACAAGACTCAGTCAGTTGACTTAAGATAGGT      300

AAAGAACCAGTTCATATTGCAAATCCCAGATTTTATATGGAAAATCTATCAGAGAAAAGAGACTCTTGGATGTAAAGAATTATGATCCTTATAAGCCCCTG
TTTCTTGGTCAAGTATAACGTTTAGGGTCTAAAATATACCTTAGATAGTCTCTTTTCTGAGAACCTACATTTCTTAATACTAGGAATATTCGGGAC      400

GACATCACACCACCTCCTGATCAGAAGGGCGAGTTCTGAAAGTGAAACAGAAGGTCTATGCCCGGACAGTGCCACAGGAGGAAGACACTGTGGAAC
CTGTAGTGTGGAGGACTAGTCTTCCCGCTCGTCAAGACTTCACTTTTGTCTTCCAGATACCGGCCTGTCACGGTGTCCTCCTTCTGTGACACCTTG      500

TCACTGAGTTTGGTATGCAGAATGTTGAAATTCCTCATCTTCCTCAAGATTTTGAAGTTGGCAAAATATAACACCTTTATATTGTGTGAACCTCTTCACCCTCC
AGTGACTCAAACCATACGTCTTACAACTTTAAGGAGTAGAAGTTCTAAAACTTCAACGTTTTATATATTGTGGAACCTCTTCACCTCCCTCC      600
```

FIG. 1b

```
CCAGGAAGCTGTGGTGGTGGAGCTTCAGTGTTCGCGGGACTCCAGGGACTGTCCTTTCCTGATATCCTCACACTTCCTCTGATGATGGCATGGAGACT
     +----+----+----+----+----+----+----+----+----+----+----+----+----+----+----+----+----+----+----+   700
GGTCCTTCGACACCACCACCTCGAAGTCACAAGCCGCCCTGAGGTCCCTGACACAGGAAAGGACTATAGGAGTGTGAAGGAGGACTACGTACCTCTGA

AGAAGACAGTTTGCTATAAAGAAAAACCTCTGAAGATGCAAGTGAATACTTTGAAAATTACATTGAAGAACTGAAGAAACAACAAGGATTTCTACTAAGAGAAC
     +----+----+----+----+----+----+----+----+----+----+----+----+----+----+----+----+----+----+----+   800
TCTTCTGTCAAACGATATATTCTTTTGGAGACTTCTACGTTCACTTATGAAACTTTTAATGTAACTTCTTGACTTCTTTGTTCCTAAAGATGATTCTCTTG

ATTTCACACCTGAAGCAACCCAATTAGCCATCTGAACAATTGCTTCAAGCATTGCTTTTGGAGGAAGTCATGAATTCAAGCACTCTGAGCCAAGAGGTGAGCGA
     +----+----+----+----+----+----+----+----+----+----+----+----+----+----+----+----+----+----+----+   900
TAAAGTGTGGACTTCGTTGGGTTAATCGGTAGACTTGTTAACGAAAACCTCCTTCAGTACTTAAGTTCGTGAGACTCGGTTCTCCACTCGCT

TTTAGTAGAGATGATTTGGGCAGAGGCCCTGGGCCCACCCTGGAACACATGCTTCTCAAGCCAGTGAACAGGATTAGCCTCAACGATGTGAGCAAGCAGAG
     +----+----+----+----+----+----+----+----+----+----+----+----+----+----+----+----+----+----+----+   1000
AAATCATCTCTACTAAACCCGTCTCCCGGGACCCCGGGTGGGACCTTGTGTACGAAGAGTTCGGTCACTTGCCTAATCGGAGTTGCTACACTCGTTCCGTCTC

GGGATTCTCCTTCTAGTAAAGGCCAGCACTGAAAAATGGAGAAACAGCAGCAATTGCAAAAGTTTTCTACTACTGATACCTCACAAAG
     +----+----+----+----+----+----+----+----+----+----+----+----+----+----+----+----+----+----+----+   1100
CCCTAAGAGGAAGATCATTTCCGGTCGTGACTTTTACCTCTCGTCGTTAACGTTTTCAAAGATGATGACTACTACTGACTATGGAGAGTTTC

GCACAATGCCCAAAAGAAGTGAACCTGGGACTATTGGCTAAGAAAAGCAGACCTCTGCCAGCTAATAAGAGACATGGTTAATGTCTGTGAAACTAATTTGTC
     +----+----+----+----+----+----+----+----+----+----+----+----+----+----+----+----+----+----+----+   1200
CGTGTTACGGGTTTCTTCACTTGGACCCTGATAACCGATTCTTTCCGTCTCTGGAGACGGTCGATTATTCTCTGTACCAATTACAGACACTTTGATTAAACAG
```

FIG. 1c

```
CAAACCCAACCACCATCCCTGCTGGCCAAATACCGAGCTTTGAGGTGCAAAATTGAGCATGTTGAACAGAATACTGAAGAATTTCTCAGGGTTAGAAAAGAG
    +---------+---------+---------+---------+---------+---------+---------+---------+---------+---------+  1300
GTTTGGGTTGGTAGGGACCGGTTTATGGCTCGAAACTCCACGTTTCTTAACTCTTGTCTTATGACTTCTTAAAGAGTCCCAATCTTTTCTC

GTTTTGCAGAATCATCACAGTAAGAGCCCAGTGGATGTCTTGCAGAGTGGCAGAGTAATGAAACCAGAGTTTTTGAGCAAACTTGGTA
    +---------+---------+---------+---------+---------+---------+---------+---------+---------+---------+  1400
CAAAACGTCTTAGTAGTGTCATTCTCGGGTCACCTACAGAACGTCTATAAATCAACCGTCTCACTTACTTTGTCTCAAAAACTCGTTTGAACCAT

ATGTGAGGCCCTTGTTGCATGGTTCTCCCTGTACAAAACATCGTGGGAATCTTGTGTCGAGGGTTGCTTTTACCCAAAGTAGTGGAAGATCGTGGTGTGCA
    +---------+---------+---------+---------+---------+---------+---------+---------+---------+---------+  1500
TACACTCCGGGAACAACGTACCAAGAGGACATGTTTTGTAGCACCCTTAGAACACAGCTCCCAACGAAAATGGGTTTCATCACCTTCTAGCACCACGT

AAGAACAGAGACGTCGGAAAACCTTGGAAGTGGGATTTATTTCAGTGATTCGGCTCAGTACAAGTACTCACACCCGGGAGAGACAGATGGCACCAGA
    +---------+---------+---------+---------+---------+---------+---------+---------+---------+---------+  1600
TTCTTGTCTGCAGCCTTTGGAACCTTCACCCTAAATAAAGTCACTAAGCGAGTCATGTTCATAGTTCATGAGTGTGGGCCCTCTGTCTACCGTGGTCT

CTCCTGCTCATTTGTGACGTAGCCCTCGGAAAAGTGTATGGACTTACATGAGAAGGACTTTCCCTTAACTGAAGCACCACCAGGCTACGACAGTGTGCATG
    +---------+---------+---------+---------+---------+---------+---------+---------+---------+---------+  1700
GAGGACGAGTAAACACTGCATCGGGAGCCTTTCACATAGTACTCTTCCTGAAAGGAATTGACTTCGTGGTGGTCCGATGCTGTCACACGTAC

GAGTTTCACAAACAGCCTCTGTCGGAGACAGTGGTCTCGAAACTCCTACTACTTAAAACAACAGATATTTTACTTTATATAATAATTTAAAAG
    +---------+---------+---------+---------+---------+---------+---------+---------+---------+---------+  1800
CTCAAAGTGTTTGTCGGAGACAGCCTCTGTCACCAGAGCTTTGAGGATGATGAATTTGTGTCTATAAAACCAATCAGGTTAAAATGAAATATATTATTTTC
```

```
CCAAGGGCCCTGTGCCTGGCACTTGTGCTGACTGGAATCCCACACAGTCGGCCGTCTTGTCCCACAGGACCTCCCAGAACCCACCTTCTGCACCCTATTGTGGC
----+----+----+----+----+----+----+----+----+----+----+----+----+----+----+----+----+----+----+----+  4300
GGTTCCCGGGACACGGACCTGAACACGACTGACCTAGGGTGTCAGCCGGCAGAACAGGGTGTCTTGGGTGGAAGACGTGGGATAACACCG

ATTGTTTTTCAGGGAGCTCATTAAGCTCTGCACAGTCTCTGCTCCACTGCAACATCCTGGAGGCTTACTACCAGGCCTTCTGCTGGCACCTTCCCTGAGC
----+----+----+----+----+----+----+----+----+----+----+----+----+----+----+----+----+----+----+----+  4400
TAACAAAAAGTCCCTCGAGTAATTCGAGACGTGTCAGACGGTGACGTTGTAGGACTCCGAAATGATGGTCCGGAAGACGACCGTGGAAGGACTCG

TGGATTCTCCCCAGCTTCATTTCTCTCTTTCCTACAGACCCTGATCCCATCAGAGGTTTTGGGTCTCTTATCATCCCTCTGCTTACTCTCCTTTTCATTTTCA
----+----+----+----+----+----+----+----+----+----+----+----+----+----+----+----+----+----+----+----+  4500
ACCTAAGAGGGGTCGAAGTAAAGAGAGAAGGATGTCTGGGACTAGGGTAGTCTCCAAAACCCAGATCTCCGAGAATGAGGAGAAAGTAAAAGT

ACCTTCCGGCAGCCTCTTTGACTGCCAACCTTAGGCTGCCAATGGCCTCTGCCTGAGGCTCTTGCAGTCAGTCCCGGACTACCCCAGTAGATCTC
----+----+----+----+----+----+----+----+----+----+----+----+----+----+----+----+----+----+----+----+  4600
TGGAAGGCGTCGGAGAAACTGACGGTTGGAATCCGACGGTTACCGGAGACGAAATGGACTCCGAGTCAGTCAGGCCTGATGGGTCATCTAGAG

TGTCTTCTAGAAGAATCAGTAGGCAGTCTCGAAGGAAGTCGATGTCCTGTCTCTTTGCCTTTCAAAAGTTCTGACACAGAAAGTGATGAGCTATCAGAAGTAC
----+----+----+----+----+----+----+----+----+----+----+----+----+----+----+----+----+----+----+----+  4700
ACAGAAGATCTTCTTAGTCATCCGTCAGAGCTTCCTTCAGCTACAGGACAGAGAAACGGAAAGTTTCAAGACTGTGTCTTCACTACTCGATAGTCTTCATG

TTCAAGACAGCTGCTTTTTACAAATAAAGTGTGATACAAAAGATGACAGTATCCCGTGCTTTCTGGAATTAAAAGAAGAGGATGAAATAGTGTGCACACA
----+----+----+----+----+----+----+----+----+----+----+----+----+----+----+----+----+----+----+----+  4800
AAGTTCTGTCGACGAAAAATGTTTATTTCACACTATGTTTTCACTGTCATAGGCACGAAAGACCTTAATTTTCTTCTACTTTATCACACGTGTGT
```

HUMAN MINOR VAULT PROTEIN P193

CROSS-REFERENCE TO RELATED APPLICATIONS

The present Application is a continuation of U.S. patent application No. 09/089,621, entitled "Human Minor Vault Protein p193,"filed Jun. 3, 1998, now U.S. Pat. No. 6,156,879, isssued Dec. 5, 2000, the contents of which is incorporated herein by reference in its entirety.

STATEMENT REGARDING FEDERALLY SPONSORED RESEARCH OR DEVELOPMENT

The present invention was made with government support under Grant No. GM 38097, awarded by the National Institutes of Health. The United States Government has certain rights in this invention.

BACKGROUND

Cancer is a major cause of morbidity and mortality in the United States. Treatment of cancer generally includes chemotherapy, radiation therapy and surgery. Unfortunately, most cancers cannot be cured using chemotherapy because tumor cells tend to develop resistance to several chemotherapeutic agents over time. These cancers are referred to as "multidrug-resistant cancers" (MDR).

Overexpression of a number of proteins has been found to be associated with MDR cells lines, including P-glycoprotein (Pgp) and multidrug resistance-associated protein (MRP). These proteins appear to mediate drug resistance by acting as cytotoxic drug efflux pumps. However, many MDR cancer cell lines are known which are not associated with overexpression of either P-glycoprotein or multidrug resistance-associated protein.

More recently, a protein has been described that is overexpressed in MDR tumor cell lines which do not overexpress either P-glycoprotein or multidrug resistance- associated protein. This protein was originally named Lung Resistance-related Protein (LRP), referring to the cell line in which it was originally identified. However, once the cDNA for Lung Resistance-related Protein was isolated and the corresponding protein sequence elucidated, it was found that Lung Resistance-related Protein was human major vault protein, a previously known protein.

Vaults are large, barrel-shaped, multi-subunit, cytoplasmic, ribonucleoprotein organelles found in virtually all higher organisms and in most normal tissues. Mammalian vaults consist of three proteins having molecular weights of approximately 210, 193 and 104, and a small RNA in the relative molar ratios of 1:1:24:4 in rats. The most abundant of these, the 104 kDa protein, is termed major vault protein (MVP) and corresponds to the Lung Resistance-related Protein. The minor vault protein p193, however, has not yet been characterized.

Therefore, there remains a need for chemotherapeutic agents that will target multidrug-resistant cancers. Further, there remains a need to characterize the minor vault protein p193.

SUMMARY

According to one embodiment of the present invention, there is provided apolynucleotide molecule encoding human minor vault protein p193, or its complementary strands, and a polynucleotide molecule which hybridizes to such a polynucleotide sequence. According to another embodiment of the present invention, there is provided a vector containing such a polynucleotide and a prokaryotic or eukaryotic host cell stably transformed or transfected by the vector.

According to yet another embodiment of the present invention, there is provided a polynucleotide molecule according to SEQ ID NO: 1, or its complementary strands, and a polynucleotide molecule which hybridizes to such a polynucleotide sequence. According to another embodiment of the present invention, there is provided a vector containing such a polynucleotide and a prokaryotic or eukaryotic host cell stably transformed or transfected by the vector.

According to still another embodiment of the present invention, there is provided a purified and isolated polynucleotide molecule consisting essentially of a nucleotide sequence encoding human minor vault protein p193, or its complementary strands, or a combination of a nucleotide sequence encoding human minor vault protein p193 and its complementary strands, as well as a polynucleotide molecule which hybridizes to such a polynucleotide sequence. According to another embodiment of the present invention, there is provided a vector containing such a polynucleotide and a prokaryotic or eukaryotic host cell stably transformed or transfected by the vector.

Additionally, there is provided a method of making human minor vault protein p193, comprising culturing a microorganism transformed with a polynucleotide according to the present invention; and recovering the human minor vault protein pl93.

FIGURES

These and other features, aspects and advantages of the present invention will become better understood with regard to the following description, appended claims, and accompanying figures where:

Figure 1D:
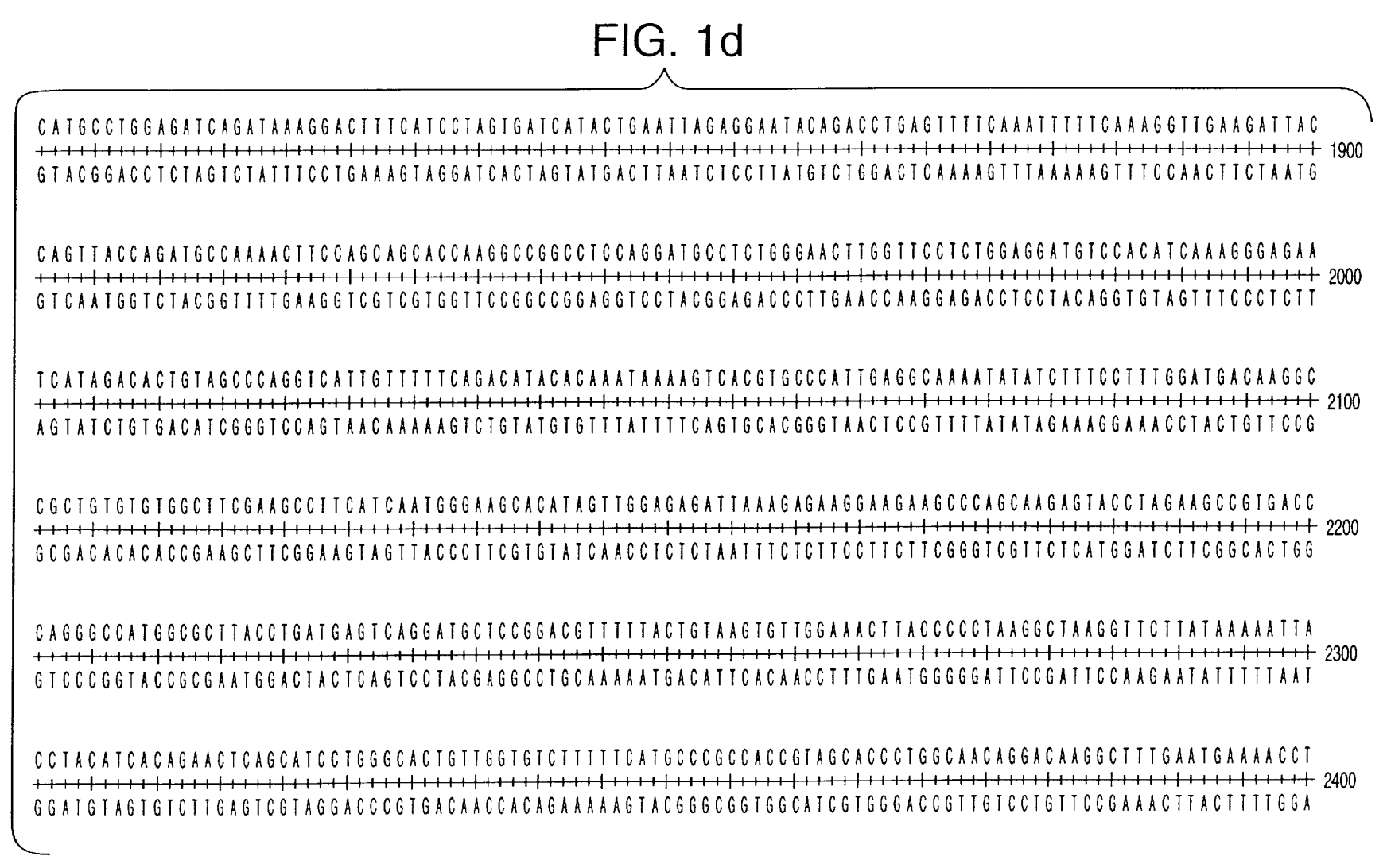
Figure 1E:
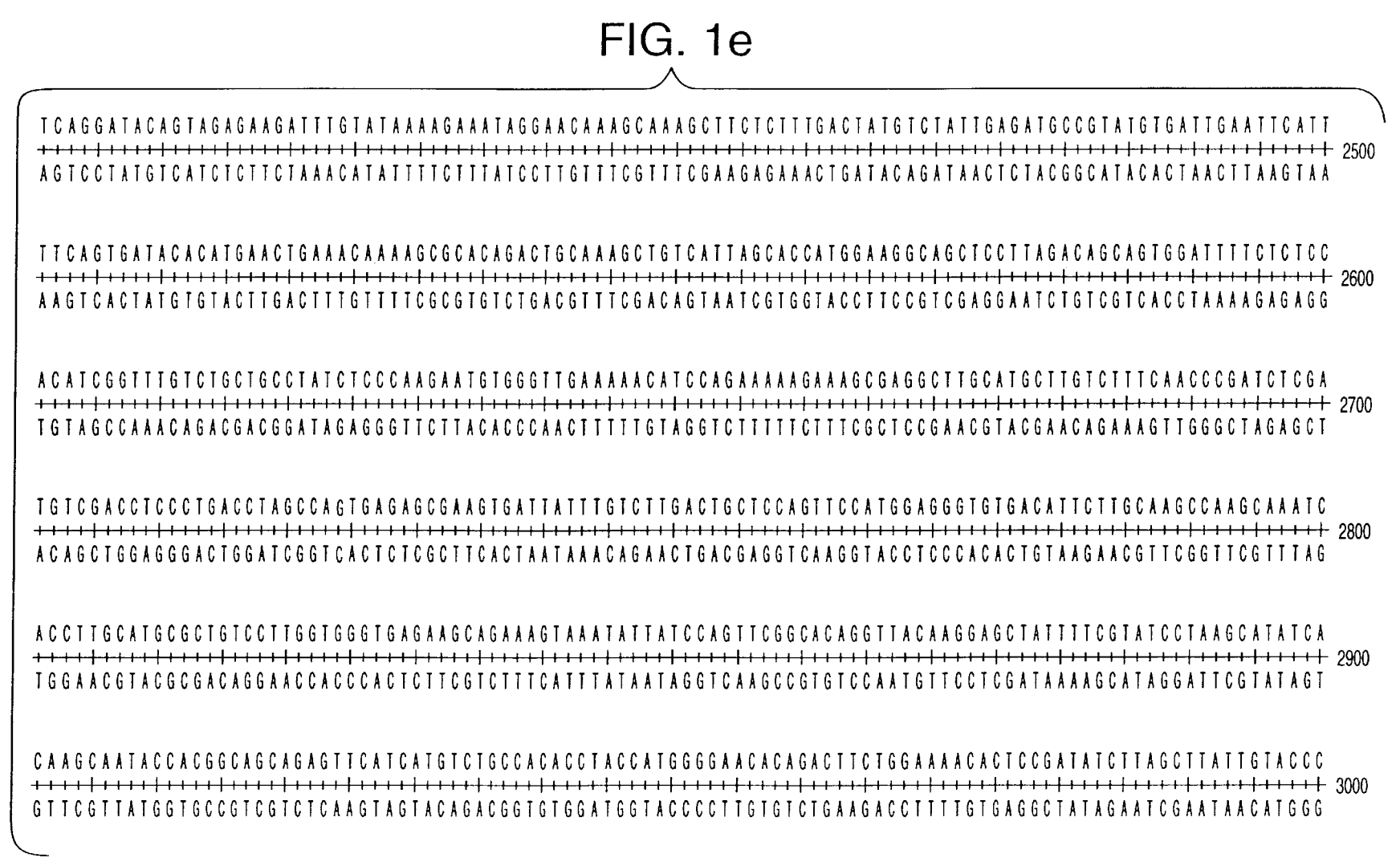
Figure 1F:
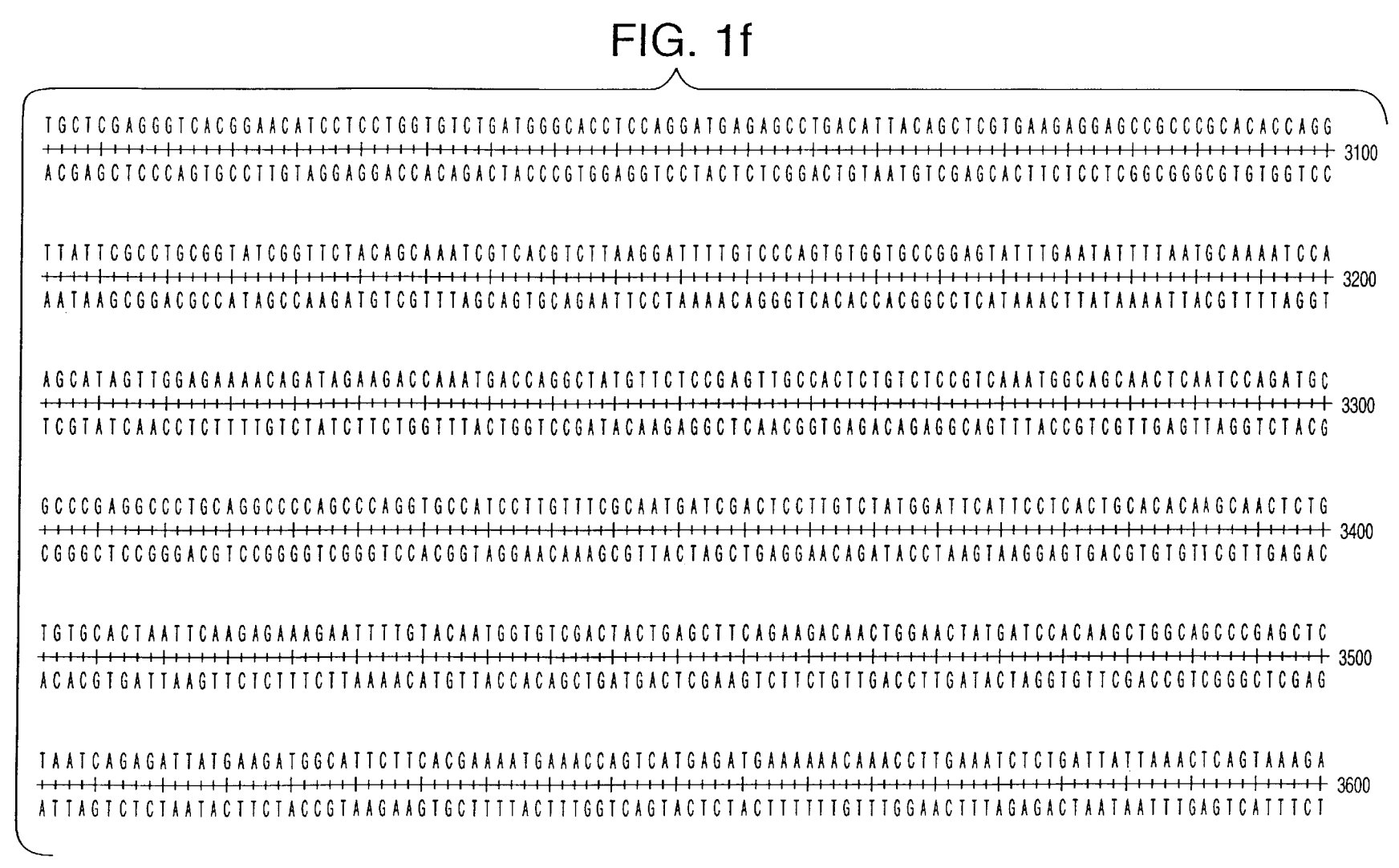
Figure 1G:
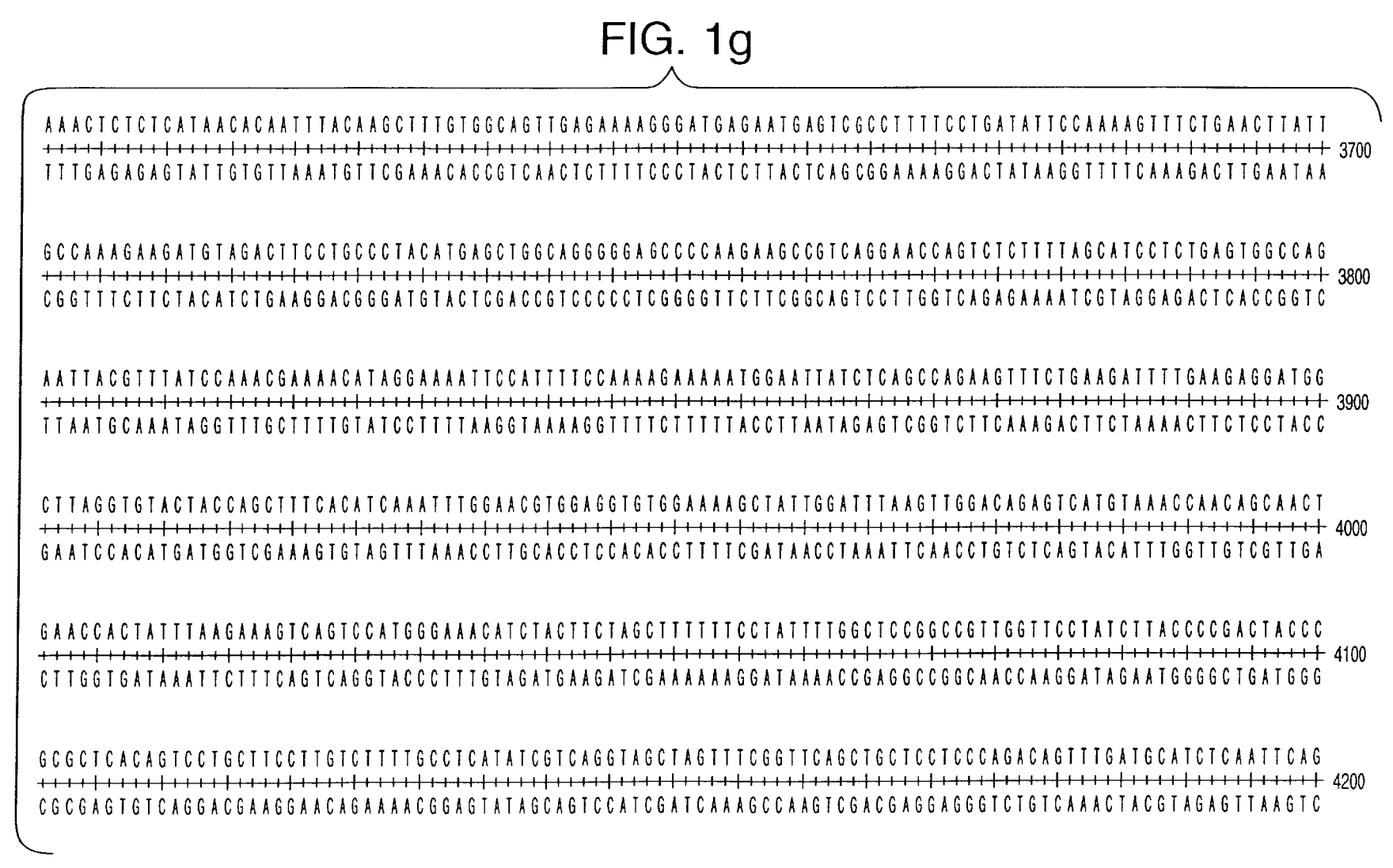
Figure 1I:
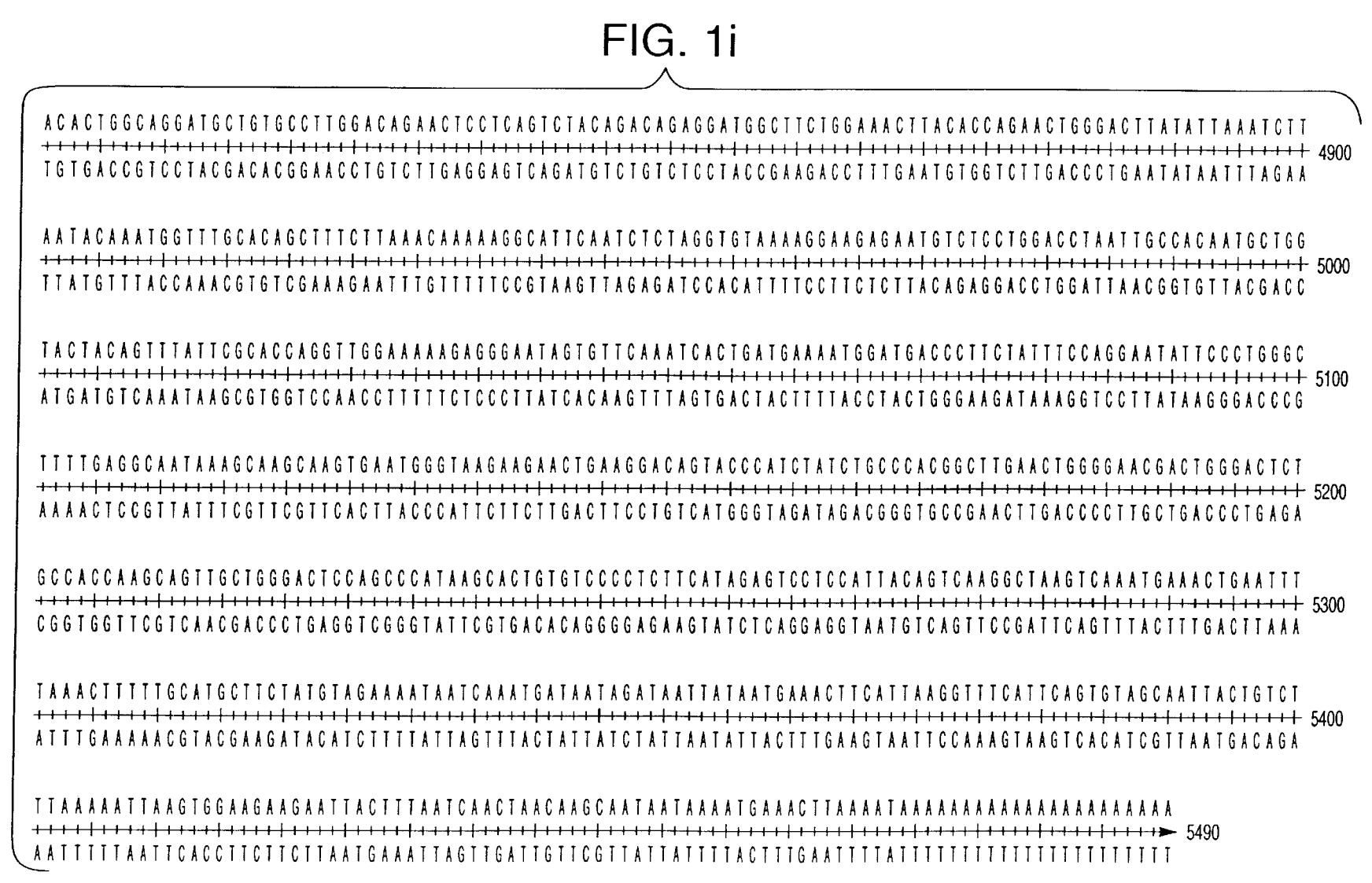

FIGS. 1a–1i show the complete sequence of cDNA encoding human minor vault protein 193 and its complementary strand, where the top strand is SEQ ID NO: 1; and FIG. 2 shows the complete amino acid sequence of human minor vault protein p193 (SEQ ID NO: 2) indicating specific regions of function.

DESCRIPTION

The present invention involves the elucidation of the amino acid sequence for human vault protein p193, as well as the DNA sequence encoding human vault protein pl93. These sequences are then utilized in methods of diagnosing multidrug resistance cancer and in methods of treating multidrug resistance cancer.

(1) Elucidation of the Human Minor Vault Protein p193 Amino Acid Sequence and the Nucleotide Sequence Encoding Human Minor Vault Protein p193:

The human minor vault protein p193 amino acid sequence and the nucleotide sequence encoding human minor vault protein p193 were elucidated as follows. First, human vault protein p193 was cloned using an interaction trap, two-hybrid system according to techniques known to those with skill in the art. See, for example, Golemis, et al., *Current Protocols in Mol. Biol.* 20.1.1–20.35 John Willey & Sons, 1997, incorporated by reference in its entirety. In summary, rat major vault protein, GenBank accession number U09870, having the 67 amino acids at the amino-terminal truncated was used as bait against a HeLa acid fusion cDNA library obtained from Roger Brent, Boston, Mass., USA to search for proteins that interacted with rat major vault protein. The interacting proteins were identified by their ability to give rise to blue colonies on media containing galactose and X-gal, a color indicator substrate. The specificity of the interaction between the identified proteins and the rat major vault protein was verified by retransformation of the identified proteins with specific, rat major vault protein and nonspecific (lexA-bicoid) bait cDNAs. This technique identified the cDNA encoding the 193 kDa minor vault protein, SEQ ID NO: 1, by its interaction with the rat major vault protein.

Referring now to FIG. 1, there is shown the complete sequence of cDNA encoding human minor vault protein p193, top strand, SEQ ID NO: 1, and its complementary strand. As can be seen, the DNA encoding human minor vault protein p193 contains 5490 base pairs. The open reading frame is from residue 107 to residue 5281.

The cDNA encoding human minor vault protein p193 was then used to deduce the amino acid sequence of the human minor vault protein p193, SEQ ID NO:2. Further, human minor vault protein p193 was purified from vaults by electrophoresis on 5% SDS-polyacrylamide gels. The gels were stained with copper (BioRad Laboratories, Hercules, Calif., USA) and the identified band was excised and destained, and the amino acids sequenced according to standard techniques using a Finnigan TSQ-7000 Triple Quadrupole Mass Spectrometer. This sequence is the same as SEQ ID NO:2.

Referring now to FIG. 2, there is shown the complete amino acid sequence of human minor vault protein p193, SEQ ID NO:2. As can be seen, the sequence includes 1724 amino acid residues.

A search of the National Center for Biotechnology databases was performed to determine if either SEQ ID NO: 1 or SEQ ID NO:2 were previously known. The search revealed a previously known nucleotide sequence, GenBank accession number D79999, having 5085 nucleotides which were identical to residues 384–5469 of SEQ ID NO: 1. GenBank accession number D79999 did not, however, include residues 107–383 of SEQ ID NO: 1 which constitutes part of the open reading frame.

The search further revealed that residues 209–563 of SEQ ID NO:2 share 28% identity to residues 609–1004, the catalytic subunit of poly (ADP-ribose) polymerase, GenBank accession number M32721, but did not otherwise reveal a homologous sequence. This catalytic subunit binds to NAD, hydrolyzes the nicotine moiety and polymerizes the ADP ribose group.

Analysis of SEQ ID NO:2 using the PROSITE protein database also revealed that residues 1–94 of SEQ ID NO:2 comprise a BRCT domain. BRCT domains refer to the C-terminus of the cancer susceptibility gene BRCA 1, and are a superfamily of conserved domains in DNA damage-response cell cycle checkpoint proteins. See, for example, Bork, et al., The Faseb J. 11:68–76, 1997; and Callebaut, I. and Mornon, J-P., FEBS Letter 400:25- 30, 1997, incorporated by reference in their entirety.

Referring again to FIG. 2, residues 1–94 of human minor vault protein p193, which comprise the BRCT domain, are indicated by the unshaded box. Residues 209–563 of human minor vault protein p193, which share 28% identity to the catalytic subunit of poly (ADP-ribose) polymerase are shown in the upper shaded box. Finally, residues 1562–1724 of human minor vault protein p193, which comprise the region necessary for interaction with human major vault protein, are shown in the lower shaded box.

(2) Generation of Antibodies to Human Minor Vault Protein pl93:

Antibodies which immunoreact with human minor vault protein p193 were produced as follows. First, fragments of human minor vault protein p193 were generated using PCR techniques. The fragments consisted of residues 408–611 and residues 1471–1724 of SEQ ID NO:2. Next, fusion proteins were generated and both polyclonal and monoclonal antibodies were produced. These antibodies recognized human minor vault protein p193 in western blots, by immunofluorescence microscopy and by immunoprecipitation.

(3) Description of Certain Embodiments of the Present Invention:

Therefore, according to the present invention, there is provided a protein consisting essentially of purified human minor vault protein p193, SEQ ID NO:2. The protein can also consist of purified biologically active variants of human minor vault protein p193 or a combination of purified human minor vault protein p193, SEQ ID NO:2, and biologically active variants of human minor vault protein pl93. In a preferred embodiment, the protein is a recombinant protein. Further, the present invention includes a protein having an amino acid sequence of greater than about 50% identity of the amino acid sequence as set forth in SEQ ID NO:2, as well as a protein recognized by a monoclonal or polyclonal antibody having affinity to a protein according to the present invention.

The protein according to the present invention can be made according to techniques known to those with skill in the art, for example, by first culturing a microorganism transformed with a polynucleotide encoding human minor vault protein pl93. Then, the human minor vault protein p193 is recovered from the microorganism.

The present invention also includes a polynucleotide molecule encoding a protein which consists essentially of human minor vault protein p193, SEQ ID NO:2, or biologically active variants of human minor vault protein p193 or a combination of purified human minor vault protein p193, SEQ ID NO:2, and biologically active variants of human minor vault protein p193, such as residues 107 to residue 5281of SEQ ID NO: 1, and includes the complementary strands to these polynucleotides and a polynucleotide molecule which hybridizes to any of the foregoing polynucleotides. The polynucleotide can be an RNA molecule or a DNA molecule, as well as other polynucleotide molecules.

According to another embodiment of the present invention, there is provided a vector containing a polynucleotide according to the present invention. The vector, such as PET 28 (available from Invitrogen, Carlsbad, Calif., USA), pGEX and pSVL (both available from Amersham Pharmacia Biotech, Piscataway, N.J., USA), can be used to stably transform or transfect a prokaryotic or eukaryotic host cell.

The present invention further includes an antibody which immunoreacts with a protein or polynucleotide according to the present invention. The Fc portion of the antibody can be selected from the group consisting of the IgM class, the IgG class and the IgA class, but can also be other classes. Preferably, the antibody is a high affinity monoclonal antibody which immunoreacts with human minor vault protein p193.

The antibody can be made, for example, by administering human minor vault protein p193 to a host in an amount sufficient to induce the production of antibodies to the human minor vault protein p193 from the antibody-producing cells. Next, the antibody- producing cells are recovered from the host and cell hybrids are formed by fusing the antibody-producing cell to cells capable of substantially unlimited reproduction. Then, the hybrids are cultured and the monoclonal antibodies are collected as a product of the hybrids. Preferably, the cells capable of substantially unlimited reproduction are myeloma cells.

EXAMPLE I
METHOD OF DIAGNOSING A PATIENT WITH A MULTIDRUG-RESISTANT CANCER

According to one embodiment of the present invention, a patient with a multidrug-resistant cancer is diagnosed by, first, providing a sample of tissue or fluid from the patient. The sample can be bone marrow, cerebral spinal fluid, blood, tears, saliva or a biopsy specimen, or can be other suitable tissue or fluid samples. Next, the level of a substance selected from the group consisting of p193 protein, p193 DNA, p193 mRNA, a substantial portion of p193 protein, a substantial portion of p193 DNA, a substantial portion of p193 MRNA and a combination of one of the foregoing in the patient sample is determined. In a preferred embodiment, the substantial portion comprises at least about 25 % of the residues of the molecule. In a particularly preferred embodiment, the substantial portion comprises at least about 50% of the residues of the molecule. Then, the level of the substance is compared to a known range of levels for the substance in patients with multidrug-resistant cancers. A diagnosis of multidrug-resistant cancer is made when the level of the substance determined is within the range of levels for the substance in patients with multidrug-resistant cancers.

EXAMPLE II
METHOD OF TREATING A PATIENT WITH MULTIDRUG-RESISTANT CANCER

According to another embodiment of the present invention, a patient with a multidrug-resistant cancer is treated by disrupting the production or function of human minor vault protein p193. This is accomplished by, for example, administering to the patient antibodies having an affinity for a substance selected from the group consisting of p193 protein and a polynucleotide encoding p193. Treatment can also be accomplished by administering to the patient at least one antisense polynucleotide having an affinity for a polynucleotide encoding p193. Further, treatment can be accomplished by administering to the patient at least one drug that blocks NAD, such as PD128763 and 3-aminobenzamide.

Although the present invention has been discussed in considerable detail with reference to certain preferred embodiments, other embodiments are possible. Therefore, the scope of the appended claims should not be limited to the description of preferred embodiments contained in this application.

---

We claim:

1. A purified polynucleotide molecule comprising the sequence of SEQ ID NO:1.

2. A purified polynucleolide molecule fully complementary to a polynucleotide sequence according to claim 1.

3. A DNA molecule according to claim 2.

4. A vector comprising the polynucleotide of claim 1.

5. An isolated prokaryotic or eukaryotic host cell stably transformed or transfected by the vector of claim 4.

6. A method of making human minor vault protein p193, comprising:

(a) culturing a microorganism transformed with a polynucleotide according to claim 1; and (b) recovering the human minor vault protein p193 which is encoded by the polynucleotide.

7. A purified polynucleotide molecule comprising the sequence of residues 107–5281 of SEQ ID NO: 1.

8. A purified polynucleotide molecule fully complementary to a polynucleotide sequence according to claim 4.

9. A DNA molecule according to claim 8.

10. A vector containing the polynucleotide of claim 7.

11. An isolated prokaryotic or eukaryotic host cell stably transformed or transfected by the vector of claim 10.

12. A method of making human minor vault protein p193, comprising:

(a) culturing a microorganism transformed with a polyaucleotide according to claim 7; and (b) recovering the human minor vault protein p193 which is encoded by the polynucleotide.

13. A purified polynucleotide molecule encoding a protein comprising SEQ ID NO:2.

14. An RNA molecule according to claim 13.

15. A DNA molecule according to claim 13.

* * * * *

UNITED STATES PATENT AND TRADEMARK OFFICE
CERTIFICATE OF CORRECTION

PATENT NO. : 6,555,347 B1
DATED : April 29, 2003
INVENTOR(S) : Leonard H. Rome and Valerie A. Kickhoefer It is certified that error appears in the above-identified patent and that said Letters Patent is hereby corrected as shown below:

Column 25,
Line 37, replace "SEQ ID NO:1 ." with -- SEQ ID NO:1. --

Column 26,
Line 36, replace "according to claim 4" with -- according to claim 7 --.

Signed and Sealed this

Twelfth Day of August, 2003

JAMES E. ROGAN
*Director of the United States Patent and Trademark Office*

SEQUENCE LISTING

```
<160> NUMBER OF SEQ ID NOS:  2

<210> SEQ ID NO 1
<211> LENGTH: 5490
<212> TYPE: DNA
<213> ORGANISM: Homo sapiens
<220> FEATURE:
<221> NAME/KEY: CDS
<222> LOCATION: (107)..(5278)

<400> SEQUENCE: 1
cgcccgccca gccccggggg cagggaaagc ctaaattacg gaattaccgc gagcaaggag         60
cgcggaatcg gggagcgtcc ggagctagct ggatcctcta ggcagg atg gtg atg          115
                                                  Met Val Met
                                                   1 gga atc ttt gca aat tgt atc ttc tgt ttg aaa gtg aag tac tta cct         163
Gly Ile Phe Ala Asn Cys Ile Phe Cys Leu Lys Val Lys Tyr Leu Pro
       5                  10                  15 cag cag cag aag aaa aag cta caa act gac att aag gaa aat ggc gga         211
Gln Gln Gln Lys Lys Lys Leu Gln Thr Asp Ile Lys Glu Asn Gly Gly
 20                  25                  30                  35 aag ttt tcc ttt tcg tta aat cct cag tgc aca cat ata atc tta gat         259
Lys Phe Ser Phe Ser Leu Asn Pro Gln Cys Thr His Ile Ile Leu Asp
                 40                  45                  50 aat gct gat gtt ctg agt cag tac caa ctg aat tct atc caa aag aac         307
Asn Ala Asp Val Leu Ser Gln Tyr Gln Leu Asn Ser Ile Gln Lys Asn
             55                  60                  65 cac gtt cat att gca aac cca gat ttt ata tgg aaa tct atc aga gaa         355
His Val His Ile Ala Asn Pro Asp Phe Ile Trp Lys Ser Ile Arg Glu
         70                  75                  80 aag aga ctc ttg gat gta aag aat tat gat cct tat aag ccc ctg gac         403
Lys Arg Leu Leu Asp Val Lys Asn Tyr Asp Pro Tyr Lys Pro Leu Asp
 85                  90                  95
```

-continued

```
atc aca cca cct cct gat cag aag gcg agc agt tct gaa gtg aaa aca         451
Ile Thr Pro Pro Pro Asp Gln Lys Ala Ser Ser Ser Glu Val Lys Thr
100             105                 110                 115 gaa ggt cta tgc ccg gac agt gcc aca gag gag gaa gac act gtg gaa         499
Glu Gly Leu Cys Pro Asp Ser Ala Thr Glu Glu Glu Asp Thr Val Glu
                120                 125                 130 ctc act gag ttt ggt atg cag aat gtt gaa att cct cat ctt cct caa         547
Leu Thr Glu Phe Gly Met Gln Asn Val Glu Ile Pro His Leu Pro Gln
        135                 140                 145 gat ttt gaa gtt gca aaa tat aac acc ttg gag aaa gtg gga atg gag         595
Asp Phe Glu Val Ala Lys Tyr Asn Thr Leu Glu Lys Val Gly Met Glu
    150                 155                 160 gga ggc cag gaa gct gtg gtg gtg gag ctt cag tgt tcg cgg gac tcc         643
Gly Gly Gln Glu Ala Val Val Val Glu Leu Gln Cys Ser Arg Asp Ser
165                 170                 175 agg gac tgt cct ttc ctg ata tcc tca cac ttc ctc ctg gat gat ggc         691
Arg Asp Cys Pro Phe Leu Ile Ser Ser His Phe Leu Leu Asp Asp Gly
180                 185                 190                 195 atg gag act aga aga cag ttt gct ata aag aaa acc tct gaa gat gca         739
Met Glu Thr Arg Arg Gln Phe Ala Ile Lys Lys Thr Ser Glu Asp Ala
                200                 205                 210 agt gaa tac ttt gaa aat tac att gaa gaa ctg aag aaa caa gga ttt         787
Ser Glu Tyr Phe Glu Asn Tyr Ile Glu Glu Leu Lys Lys Gln Gly Phe
        215                 220                 225 cta cta aga gaa cat ttc aca cct gaa gca acc caa tta gca tct gaa         835
Leu Leu Arg Glu His Phe Thr Pro Glu Ala Thr Gln Leu Ala Ser Glu
    230                 235                 240 caa ttg caa gca ttg ctt ttg gag gaa gtc atg aat tca agc act ctg         883
Gln Leu Gln Ala Leu Leu Leu Glu Glu Val Met Asn Ser Ser Thr Leu
245                 250                 255 agc caa gag gtg agc gat tta gta gag atg att tgg gca gag gcc ctg         931
Ser Gln Glu Val Ser Asp Leu Val Glu Met Ile Trp Ala Glu Ala Leu
260                 265                 270                 275 ggc cac ctg gaa cac atg ctt ctc aag cca gtg aac agg att agc ctc         979
Gly His Leu Glu His Met Leu Leu Lys Pro Val Asn Arg Ile Ser Leu
                280                 285                 290 aac gat gtg agc aag gca gag ggg att ctc ctt cta gta aag gca gca        1027
Asn Asp Val Ser Lys Ala Glu Gly Ile Leu Leu Leu Val Lys Ala Ala
        295                 300                 305 ctg aaa aat gga gaa aca gca gag caa ttg caa aag atg atg aca gag        1075
Leu Lys Asn Gly Glu Thr Ala Glu Gln Leu Gln Lys Met Met Thr Glu
    310                 315                 320 ttt tac aga ctg ata cct cac aaa ggc aca atg ccc aaa gaa gtg aac        1123
Phe Tyr Arg Leu Ile Pro His Lys Gly Thr Met Pro Lys Glu Val Asn
325                 330                 335 ctg gga cta ttg gct aag aaa gca gac ctc tgc cag cta ata aga gac        1171
Leu Gly Leu Leu Ala Lys Lys Ala Asp Leu Cys Gln Leu Ile Arg Asp
340                 345                 350                 355 atg gtt aat gtc tgt gaa act aat ttg tcc aaa ccc aac cca cca tcc        1219
Met Val Asn Val Cys Glu Thr Asn Leu Ser Lys Pro Asn Pro Pro Ser
                360                 365                 370 ctg gcc aaa tac cga gct ttg agg tgc aaa att gag cat gtt gaa cag        1267
Leu Ala Lys Tyr Arg Ala Leu Arg Cys Lys Ile Glu His Val Glu Gln
        375                 380                 385 aat act gaa gaa ttt ctc agg gtt aga aaa gag gtt ttg cag aat cat        1315
Asn Thr Glu Glu Phe Leu Arg Val Arg Lys Glu Val Leu Gln Asn His
    390                 395                 400 cac agt aag agc cca gtg gat gtc ttg cag ata ttt aga gtt ggc aga        1363
His Ser Lys Ser Pro Val Asp Val Leu Gln Ile Phe Arg Val Gly Arg
405                 410                 415
```

```
                                                        -continued gtg aat gaa acc aca gag ttt ttg agc aaa ctt ggt aat gtg agg ccc      1411
Val Asn Glu Thr Thr Glu Phe Leu Ser Lys Leu Gly Asn Val Arg Pro
420                 425                 430                 435 ttg ttg cat ggt tct cct gta caa aac atc gtg gga atc ttg tgt cga      1459
Leu Leu His Gly Ser Pro Val Gln Asn Ile Val Gly Ile Leu Cys Arg
                440                 445                 450 ggg ttg ctt tta ccc aaa gta gtg gaa gat cgt ggt gtg caa aga aca      1507
Gly Leu Leu Leu Pro Lys Val Val Glu Asp Arg Gly Val Gln Arg Thr
            455                 460                 465 gac gtc gga aac ctt gga agt ggg att tat ttc agt gat tcg ctc agt      1555
Asp Val Gly Asn Leu Gly Ser Gly Ile Tyr Phe Ser Asp Ser Leu Ser
        470                 475                 480 aca agt atc aag tac tca cac ccg gga gag aca gat ggc acc aga ctc      1603
Thr Ser Ile Lys Tyr Ser His Pro Gly Glu Thr Asp Gly Thr Arg Leu
    485                 490                 495 ctg ctc att tgt gac gta gcc ctc gga aag tgt atg gac tta cat gag      1651
Leu Leu Ile Cys Asp Val Ala Leu Gly Lys Cys Met Asp Leu His Glu
500                 505                 510                 515 aag gac ttt ccc tta act gaa gca cca cca ggc tac gac agt gtg cat      1699
Lys Asp Phe Pro Leu Thr Glu Ala Pro Pro Gly Tyr Asp Ser Val His
                520                 525                 530 gga gtt tca caa aca gcc tct gtc acc aca gac ttt gag gat gat gaa      1747
Gly Val Ser Gln Thr Ala Ser Val Thr Thr Asp Phe Glu Asp Asp Glu
            535                 540                 545 ttt gtt gtc tat aaa acc aat cag gtt aaa atg aaa tat att att aaa      1795
Phe Val Val Tyr Lys Thr Asn Gln Val Lys Met Lys Tyr Ile Ile Lys
        550                 555                 560 ttt tcc atg cct gga gat cag ata aag gac ttt cat cct agt gat cat      1843
Phe Ser Met Pro Gly Asp Gln Ile Lys Asp Phe His Pro Ser Asp His
    565                 570                 575 act gaa tta gag gaa tac aga cct gag ttt tca aat ttt tca aag gtt      1891
Thr Glu Leu Glu Glu Tyr Arg Pro Glu Phe Ser Asn Phe Ser Lys Val
580                 585                 590                 595 gaa gat tac cag tta cca gat gcc aaa act tcc agc agc acc aag gcc      1939
Glu Asp Tyr Gln Leu Pro Asp Ala Lys Thr Ser Ser Ser Thr Lys Ala
                600                 605                 610 ggc ctc cag gat gcc tct ggg aac ttg gtt cct ctg gag gat gtc cac      1987
Gly Leu Gln Asp Ala Ser Gly Asn Leu Val Pro Leu Glu Asp Val His
            615                 620                 625 atc aaa ggg aga atc ata gac act gta gcc cag gtc att gtt ttt cag      2035
Ile Lys Gly Arg Ile Ile Asp Thr Val Ala Gln Val Ile Val Phe Gln
        630                 635                 640 aca tac aca aat aaa agt cac gtg ccc att gag gca aaa tat atc ttt      2083
Thr Tyr Thr Asn Lys Ser His Val Pro Ile Glu Ala Lys Tyr Ile Phe
    645                 650                 655 cct ttg gat gac aag gcc gct gtg tgt ggc ttc gaa gcc ttc atc aat      2131
Pro Leu Asp Asp Lys Ala Ala Val Cys Gly Phe Glu Ala Phe Ile Asn
660                 665                 670                 675 ggg aag cac ata gtt gga gag att aaa gag aag gaa gaa gcc cag caa      2179
Gly Lys His Ile Val Gly Glu Ile Lys Glu Lys Glu Glu Ala Gln Gln
                680                 685                 690 gag tac cta gaa gcc gtg acc cag ggc cat ggc gct tac ctg atg agt      2227
Glu Tyr Leu Glu Ala Val Thr Gln Gly His Gly Ala Tyr Leu Met Ser
            695                 700                 705 cag gat gct ccg gac gtt ttt act gta agt gtt gga aac tta ccc cct      2275
Gln Asp Ala Pro Asp Val Phe Thr Val Ser Val Gly Asn Leu Pro Pro
        710                 715                 720 aag gct aag gtt ctt ata aaa att acc tac atc aca gaa ctc agc atc      2323
Lys Ala Lys Val Leu Ile Lys Ile Thr Tyr Ile Thr Glu Leu Ser Ile
```

|  |  |  |  |  |  |  |  |  |  |  |  |  |  |  |  |
|---|---|---|---|---|---|---|---|---|---|---|---|---|---|---|---|
| 725 | | | | | 730 | | | | | 735 | | | | | |

| ctg | ggc | act | gtt | ggt | gtc | ttt | ttc | atg | ccc | gcc | acc | gta | gca | ccc | tgg | 2371 |
|---|---|---|---|---|---|---|---|---|---|---|---|---|---|---|---|---|
| Leu | Gly | Thr | Val | Gly | Val | Phe | Phe | Met | Pro | Ala | Thr | Val | Ala | Pro | Trp | |
| 740 | | | | | 745 | | | | | 750 | | | | | 755 | |

| caa | cag | gac | aag | gct | ttg | aat | gaa | aac | ctt | cag | gat | aca | gta | gag | aag | 2419 |
|---|---|---|---|---|---|---|---|---|---|---|---|---|---|---|---|---|
| Gln | Gln | Asp | Lys | Ala | Leu | Asn | Glu | Asn | Leu | Gln | Asp | Thr | Val | Glu | Lys | |
| | | | 760 | | | | | 765 | | | | | 770 | | | |

| att | tgt | ata | aaa | gaa | ata | gga | aca | aag | caa | agc | ttc | tct | ttg | act | atg | 2467 |
|---|---|---|---|---|---|---|---|---|---|---|---|---|---|---|---|---|
| Ile | Cys | Ile | Lys | Glu | Ile | Gly | Thr | Lys | Gln | Ser | Phe | Ser | Leu | Thr | Met | |
| | | 775 | | | | | 780 | | | | | 785 | | | | |

| tct | att | gag | atg | ccg | tat | gtg | att | gaa | ttc | att | ttc | agt | gat | aca | cat | 2515 |
|---|---|---|---|---|---|---|---|---|---|---|---|---|---|---|---|---|
| Ser | Ile | Glu | Met | Pro | Tyr | Val | Ile | Glu | Phe | Ile | Phe | Ser | Asp | Thr | His | |
| | | 790 | | | | | 795 | | | | | 800 | | | | |

| gaa | ctg | aaa | caa | aag | cgc | aca | gac | tgc | aaa | gct | gtc | att | agc | acc | atg | 2563 |
|---|---|---|---|---|---|---|---|---|---|---|---|---|---|---|---|---|
| Glu | Leu | Lys | Gln | Lys | Arg | Thr | Asp | Cys | Lys | Ala | Val | Ile | Ser | Thr | Met | |
| | | 805 | | | | | 810 | | | | | 815 | | | | |

| gaa | ggc | agc | tcc | tta | gac | agc | agt | gga | ttt | tct | ctc | cac | atc | ggt | ttg | 2611 |
|---|---|---|---|---|---|---|---|---|---|---|---|---|---|---|---|---|
| Glu | Gly | Ser | Ser | Leu | Asp | Ser | Ser | Gly | Phe | Ser | Leu | His | Ile | Gly | Leu | |
| 820 | | | | | 825 | | | | | 830 | | | | | 835 | |

| tct | gct | gcc | tat | ctc | cca | aga | atg | tgg | gtt | gaa | aaa | cat | cca | gaa | aaa | 2659 |
|---|---|---|---|---|---|---|---|---|---|---|---|---|---|---|---|---|
| Ser | Ala | Ala | Tyr | Leu | Pro | Arg | Met | Trp | Val | Glu | Lys | His | Pro | Glu | Lys | |
| | | | 840 | | | | | 845 | | | | | 850 | | | |

| gaa | agc | gag | gct | tgc | atg | ctt | gtc | ttt | caa | ccc | gat | ctc | gat | gtc | gac | 2707 |
|---|---|---|---|---|---|---|---|---|---|---|---|---|---|---|---|---|
| Glu | Ser | Glu | Ala | Cys | Met | Leu | Val | Phe | Gln | Pro | Asp | Leu | Asp | Val | Asp | |
| | | | 855 | | | | | 860 | | | | | 865 | | | |

| ctc | cct | gac | cta | gcc | agt | gag | agc | gaa | gtg | att | att | tgt | ctt | gac | tgc | 2755 |
|---|---|---|---|---|---|---|---|---|---|---|---|---|---|---|---|---|
| Leu | Pro | Asp | Leu | Ala | Ser | Glu | Ser | Glu | Val | Ile | Ile | Cys | Leu | Asp | Cys | |
| | | 870 | | | | | 875 | | | | | 880 | | | | |

| tcc | agt | tcc | atg | gag | ggt | gtg | aca | ttc | ttg | caa | gcc | aag | caa | atc | acc | 2803 |
|---|---|---|---|---|---|---|---|---|---|---|---|---|---|---|---|---|
| Ser | Ser | Ser | Met | Glu | Gly | Val | Thr | Phe | Leu | Gln | Ala | Lys | Gln | Ile | Thr | |
| 885 | | | | | 890 | | | | | 895 | | | | | | |

| ttg | cat | gcg | ctg | tcc | ttg | gtg | ggt | gag | aag | cag | aaa | gta | aat | att | atc | 2851 |
|---|---|---|---|---|---|---|---|---|---|---|---|---|---|---|---|---|
| Leu | His | Ala | Leu | Ser | Leu | Val | Gly | Glu | Lys | Gln | Lys | Val | Asn | Ile | Ile | |
| 900 | | | | | 905 | | | | | 910 | | | | | 915 | |

| cag | ttc | ggc | aca | ggt | tac | aag | gag | cta | ttt | tcg | tat | cct | aag | cat | atc | 2899 |
|---|---|---|---|---|---|---|---|---|---|---|---|---|---|---|---|---|
| Gln | Phe | Gly | Thr | Gly | Tyr | Lys | Glu | Leu | Phe | Ser | Tyr | Pro | Lys | His | Ile | |
| | | | 920 | | | | | 925 | | | | | 930 | | | |

| aca | agc | aat | acc | acg | gca | gca | gag | ttc | atc | atg | tct | gcc | aca | cct | acc | 2947 |
|---|---|---|---|---|---|---|---|---|---|---|---|---|---|---|---|---|
| Thr | Ser | Asn | Thr | Thr | Ala | Ala | Glu | Phe | Ile | Met | Ser | Ala | Thr | Pro | Thr | |
| | | | 935 | | | | | 940 | | | | | 945 | | | |

| atg | ggg | aac | aca | gac | ttc | tgg | aaa | aca | ctc | cga | tat | ctt | agc | tta | ttg | 2995 |
|---|---|---|---|---|---|---|---|---|---|---|---|---|---|---|---|---|
| Met | Gly | Asn | Thr | Asp | Phe | Trp | Lys | Thr | Leu | Arg | Tyr | Leu | Ser | Leu | Leu | |
| | | | 950 | | | | | 955 | | | | | 960 | | | |

| tac | cct | gct | cga | ggg | tca | cgg | aac | atc | ctc | ctg | gtg | tct | gat | ggg | cac | 3043 |
|---|---|---|---|---|---|---|---|---|---|---|---|---|---|---|---|---|
| Tyr | Pro | Ala | Arg | Gly | Ser | Arg | Asn | Ile | Leu | Leu | Val | Ser | Asp | Gly | His | |
| | 965 | | | | | 970 | | | | | 975 | | | | | |

| ctc | cag | gat | gag | agc | ctg | aca | tta | cag | ctc | gtg | aag | agg | agc | cgc | ccg | 3091 |
|---|---|---|---|---|---|---|---|---|---|---|---|---|---|---|---|---|
| Leu | Gln | Asp | Glu | Ser | Leu | Thr | Leu | Gln | Leu | Val | Lys | Arg | Ser | Arg | Pro | |
| 980 | | | | | 985 | | | | | 990 | | | | | 995 | |

| cac | acc | agg | tta | ttc | gcc | tgc | ggt | atc | ggt | tct | aca | gca | aat | cgt | cac | 3139 |
|---|---|---|---|---|---|---|---|---|---|---|---|---|---|---|---|---|
| His | Thr | Arg | Leu | Phe | Ala | Cys | Gly | Ile | Gly | Ser | Thr | Ala | Asn | Arg | His | |
| | | | 1000 | | | | | 1005 | | | | | 1010 | | | |

| gtc | tta | agg | att | ttg | tcc | cag | tgt | ggt | gcc | gga | gta | ttt | gaa | tat | ttt | 3187 |
|---|---|---|---|---|---|---|---|---|---|---|---|---|---|---|---|---|
| Val | Leu | Arg | Ile | Leu | Ser | Gln | Cys | Gly | Ala | Gly | Val | Phe | Glu | Tyr | Phe | |
| | | | 1015 | | | | | 1020 | | | | | 1025 | | | |

| aat | gca | aaa | tcc | aag | cat | agt | tgg | aga | aaa | cag | ata | gaa | gac | caa | atg | 3235 |
|---|---|---|---|---|---|---|---|---|---|---|---|---|---|---|---|---|
| Asn | Ala | Lys | Ser | Lys | His | Ser | Trp | Arg | Lys | Gln | Ile | Glu | Asp | Gln | Met | |
| | | | 1030 | | | | | 1035 | | | | | 1040 | | | |

| acc | agg | cta | tgt | tct | ccg | agt | tgc | cac | tct | gtc | tcc | gtc | aaa | tgg | cag | 3283 |
|---|---|---|---|---|---|---|---|---|---|---|---|---|---|---|---|---|

-continued

```
                Thr Arg Leu Cys Ser Pro Ser Cys His Ser Val Ser Val Lys Trp Gln
                    1045                1050                1055 caa ctc aat cca gat gcg ccc gag gcc ctg cag gcc cca gcc cag gtg        3331
Gln Leu Asn Pro Asp Ala Pro Glu Ala Leu Gln Ala Pro Ala Gln Val
1060                1065                1070                1075 cca tcc ttg ttt cgc aat gat cga ctc ctt gtc tat gga ttc att cct        3379
Pro Ser Leu Phe Arg Asn Asp Arg Leu Leu Val Tyr Gly Phe Ile Pro
                1080                1085                1090 cac tgc aca caa gca act ctg tgt gca cta att caa gag aaa gaa ttt        3427
His Cys Thr Gln Ala Thr Leu Cys Ala Leu Ile Gln Glu Lys Glu Phe
            1095                1100                1105 tgt aca atg gtg tcg act act gag ctt cag aag aca act gga act atg        3475
Cys Thr Met Val Ser Thr Thr Glu Leu Gln Lys Thr Thr Gly Thr Met
    1110                1115                1120 atc cac aag ctg gca gcc cga gct cta atc aga gat tat gaa gat ggc        3523
Ile His Lys Leu Ala Ala Arg Ala Leu Ile Arg Asp Tyr Glu Asp Gly
1125                1130                1135 att ctt cac gaa aat gaa acc agt cat gag atg aaa aaa caa acc ttg        3571
Ile Leu His Glu Asn Glu Thr Ser His Glu Met Lys Lys Gln Thr Leu
1140                1145                1150                1155 aaa tct ctg att att aaa ctc agt aaa gaa aac tct ctc ata aca caa        3619
Lys Ser Leu Ile Ile Lys Leu Ser Lys Glu Asn Ser Leu Ile Thr Gln
                1160                1165                1170 ttt aca agc ttt gtg gca gtt gag aaa agg gat gag aat gag tcg cct        3667
Phe Thr Ser Phe Val Ala Val Glu Lys Arg Asp Glu Asn Glu Ser Pro
            1175                1180                1185 ttt cct gat att cca aaa gtt tct gaa ctt att gcc aaa gaa gat gta        3715
Phe Pro Asp Ile Pro Lys Val Ser Glu Leu Ile Ala Lys Glu Asp Val
        1190                1195                1200 gac ttc ctg ccc tac atg agc tgg cag ggg gag ccc caa gaa gcc gtc        3763
Asp Phe Leu Pro Tyr Met Ser Trp Gln Gly Glu Pro Gln Glu Ala Val
    1205                1210                1215 agg aac cag tct ctt tta gca tcc tct gag tgg cca gaa tta cgt tta        3811
Arg Asn Gln Ser Leu Leu Ala Ser Ser Glu Trp Pro Glu Leu Arg Leu
1220                1225                1230                1235 tcc aaa cga aaa cat agg aaa att cca ttt tcc aaa aga aaa atg gaa        3859
Ser Lys Arg Lys His Arg Lys Ile Pro Phe Ser Lys Arg Lys Met Glu
                1240                1245                1250 tta tct cag cca gaa gtt tct gaa gat ttt gaa gag gat ggc tta ggt        3907
Leu Ser Gln Pro Glu Val Ser Glu Asp Phe Glu Glu Asp Gly Leu Gly
            1255                1260                1265 gta cta cca gct ttc aca tca aat ttg gaa cgt gga ggt gtg gaa aag        3955
Val Leu Pro Ala Phe Thr Ser Asn Leu Glu Arg Gly Gly Val Glu Lys
        1270                1275                1280 cta ttg gat tta agt tgg aca gag tca tgt aaa cca aca gca act gaa        4003
Leu Leu Asp Leu Ser Trp Thr Glu Ser Cys Lys Pro Thr Ala Thr Glu
    1285                1290                1295 cca cta ttt aag aaa gtc agt cca tgg gaa aca tct act tct agc ttt        4051
Pro Leu Phe Lys Lys Val Ser Pro Trp Glu Thr Ser Thr Ser Ser Phe
1300                1305                1310                1315 ttt cct att ttg gct ccg gcc gtt ggt tcc tat ctt acc ccg act acc        4099
Phe Pro Ile Leu Ala Pro Ala Val Gly Ser Tyr Leu Thr Pro Thr Thr
                1320                1325                1330 cgc gct cac agt cct gct tcc ttg tct ttt gcc tca tat cgt cag gta        4147
Arg Ala His Ser Pro Ala Ser Leu Ser Phe Ala Ser Tyr Arg Gln Val
            1335                1340                1345 gct agt ttc ggt tca gct gct cct ccc aga cag ttt gat gca tct caa        4195
Ala Ser Phe Gly Ser Ala Ala Pro Pro Arg Gln Phe Asp Ala Ser Gln
        1350                1355                1360
```

-continued

| | |
|---|---|
| ttc agc caa ggc cct gtg cct ggc act tgt gct gac tgg atc cca cag<br>Phe Ser Gln Gly Pro Val Pro Gly Thr Cys Ala Asp Trp Ile Pro Gln<br>1365                  1370                  1375 | 4243 |
| tcg gcg tct tgt ccc aca gga cct ccc cag aac cca cct tct gca ccc<br>Ser Ala Ser Cys Pro Thr Gly Pro Pro Gln Asn Pro Pro Ser Ala Pro<br>1380                1385                1390                1395 | 4291 |
| tat tgt ggc att gtt ttt tca ggg agc tca tta agc tct gca cag tct<br>Tyr Cys Gly Ile Val Phe Ser Gly Ser Ser Leu Ser Ser Ala Gln Ser<br>                1400                1405                1410 | 4339 |
| gct cca ctg caa cat cct gga ggc ttt act acc agg cct tct gct ggc<br>Ala Pro Leu Gln His Pro Gly Gly Phe Thr Thr Arg Pro Ser Ala Gly<br>1415                  1420                1425 | 4387 |
| acc ttc cct gag ctg gat tct ccc cag ctt cat ttc tct ctt cct aca<br>Thr Phe Pro Glu Leu Asp Ser Pro Gln Leu His Phe Ser Leu Pro Thr<br>1430                  1435                1440 | 4435 |
| gac cct gat ccc atc aga ggt ttt ggg tct tat cat ccc tct gct tac<br>Asp Pro Asp Pro Ile Arg Gly Phe Gly Ser Tyr His Pro Ser Ala Tyr<br>1445                  1450                1455 | 4483 |
| tct cct ttt cat ttt caa cct tcc gca gcc tct ttg act gca aac ctt<br>Ser Pro Phe His Phe Gln Pro Ser Ala Ala Ser Leu Thr Ala Asn Leu<br>1460                1465                1470                1475 | 4531 |
| agg ctg cca atg gcc tct gct tta cct gag gct ctt tgc agt cag tcc<br>Arg Leu Pro Met Ala Ser Ala Leu Pro Glu Ala Leu Cys Ser Gln Ser<br>                1480                1485                1490 | 4579 |
| cgg act acc cca gta gat ctc tgt ctt cta gaa gaa tca gta ggc agt<br>Arg Thr Thr Pro Val Asp Leu Cys Leu Leu Glu Glu Ser Val Gly Ser<br>1495                  1500                1505 | 4627 |
| ctc gaa gga agt cga tgt cct gtc ttt gct ttt caa agt tct gac aca<br>Leu Glu Gly Ser Arg Cys Pro Val Phe Ala Phe Gln Ser Ser Asp Thr<br>1510                  1515                1520 | 4675 |
| gaa agt gat gag cta tca gaa gta ctt caa gac agc tgc ttt tta caa<br>Glu Ser Asp Glu Leu Ser Glu Val Leu Gln Asp Ser Cys Phe Leu Gln<br>1525                  1530                1535 | 4723 |
| ata aag tgt gat aca aaa gat gac agt atc ccg tgc ttt ctg gaa tta<br>Ile Lys Cys Asp Thr Lys Asp Asp Ser Ile Pro Cys Phe Leu Glu Leu<br>1540                  1545                1550                1555 | 4771 |
| aaa gaa gag gat gaa ata gtg tgc aca caa cac tgg cag gat gct gtg<br>Lys Glu Glu Asp Glu Ile Val Cys Thr Gln His Trp Gln Asp Ala Val<br>                1560                1565                1570 | 4819 |
| cct tgg aca gaa ctc ctc agt cta cag aca gag gat ggc ttc tgg aaa<br>Pro Trp Thr Glu Leu Leu Ser Leu Gln Thr Glu Asp Gly Phe Trp Lys<br>1575                  1580                1585 | 4867 |
| ctt aca cca gaa ctg gga ctt ata tta aat ctt aat aca aat ggt ttg<br>Leu Thr Pro Glu Leu Gly Leu Ile Leu Asn Leu Asn Thr Asn Gly Leu<br>1590                  1595                1600 | 4915 |
| cac agc ttt ctt aaa caa aaa ggc att caa tct cta ggt gta aaa gga<br>His Ser Phe Leu Lys Gln Lys Gly Ile Gln Ser Leu Gly Val Lys Gly<br>1605                  1610                1615 | 4963 |
| aga gaa tgt ctc ctg gac cta att gcc aca atg ctg gta cta cag ttt<br>Arg Glu Cys Leu Leu Asp Leu Ile Ala Thr Met Leu Val Leu Gln Phe<br>1620                  1625                1630                1635 | 5011 |
| att cgc acc agg ttg gaa aaa gag gga ata gtg ttc aaa tca ctg atg<br>Ile Arg Thr Arg Leu Glu Lys Glu Gly Ile Val Phe Lys Ser Leu Met<br>                1640                1645                1650 | 5059 |
| aaa atg gat gac cct tct att tcc agg aat att ccc tgg gct ttt gag<br>Lys Met Asp Asp Pro Ser Ile Ser Arg Asn Ile Pro Trp Ala Phe Glu<br>1655                  1660                1665 | 5107 |
| gca ata aag caa gca agt gaa tgg gta aga aga act gaa gga cag tac<br>Ala Ile Lys Gln Ala Ser Glu Trp Val Arg Arg Thr Glu Gly Gln Tyr<br>1670                  1675                1680 | 5155 |

```
cca tct atc tgc cca cgg ctt gaa ctg ggg aac gac tgg gac tct gcc      5203
Pro Ser Ile Cys Pro Arg Leu Glu Leu Gly Asn Asp Trp Asp Ser Ala
    1685            1690                1695 acc aag cag ttg ctg gga ctc cag ccc ata agc act gtg tcc cct ctt      5251
Thr Lys Gln Leu Leu Gly Leu Gln Pro Ile Ser Thr Val Ser Pro Leu
1700            1705                1710                1715 cat aga gtc ctc cat tac agt caa ggc taagtcaaat gaaactgaat            5298
His Arg Val Leu His Tyr Ser Gln Gly
                1720 tttaaacttt ttgcatgctt ctatgtagaa aataatcaaa tgataataga taattataat    5358 gaaacttcat taaggtttca ttcagtgtag caattactgt ctttaaaaat taagtggaag    5418 aagaattact ttaatcaact aacaagcaat aataaaatga aacttaaaat aaaaaaaaaa    5478 aaaaaaaaaa aa                                                        5490

<210> SEQ ID NO 2
<211> LENGTH: 1724
<212> TYPE: PRT
<213> ORGANISM: Homo sapiens

<400> SEQUENCE: 2

Met Val Met Gly Ile Phe Ala Asn Cys Ile Phe Cys Leu Lys Val Lys
 1               5                  10                  15

Tyr Leu Pro Gln Gln Lys Lys Leu Gln Thr Asp Ile Lys Glu
                20                  25                  30

Asn Gly Gly Lys Phe Ser Phe Ser Leu Asn Pro Gln Cys Thr His Ile
            35                  40                  45

Ile Leu Asp Asn Ala Asp Val Leu Ser Gln Tyr Gln Leu Asn Ser Ile
    50                  55                  60

Gln Lys Asn His Val His Ile Ala Asn Pro Asp Phe Ile Trp Lys Ser
65                  70                  75                  80

Ile Arg Glu Lys Arg Leu Leu Asp Val Lys Asn Tyr Asp Pro Tyr Lys
                85                  90                  95

Pro Leu Asp Ile Thr Pro Pro Asp Gln Lys Ala Ser Ser Ser Glu
            100                 105                 110

Val Lys Thr Glu Gly Leu Cys Pro Asp Ser Ala Thr Glu Glu Glu Asp
        115                 120                 125

Thr Val Glu Leu Thr Glu Phe Gly Met Gln Asn Val Glu Ile Pro His
130                 135                 140

Leu Pro Gln Asp Phe Glu Val Ala Lys Tyr Asn Thr Leu Glu Lys Val
145                 150                 155                 160

Gly Met Glu Gly Gly Gln Glu Ala Val Val Glu Leu Gln Cys Ser
                165                 170                 175

Arg Asp Ser Arg Asp Cys Pro Phe Leu Ile Ser Ser His Phe Leu Leu
            180                 185                 190

Asp Asp Gly Met Glu Thr Arg Arg Gln Phe Ala Ile Lys Lys Thr Ser
        195                 200                 205

Glu Asp Ala Ser Glu Tyr Phe Glu Asn Tyr Ile Glu Glu Leu Lys Lys
    210                 215                 220

Gln Gly Phe Leu Leu Arg Glu His Phe Thr Pro Glu Ala Thr Gln Leu
225                 230                 235                 240

Ala Ser Glu Gln Leu Gln Ala Leu Leu Glu Glu Val Met Asn Ser
                245                 250                 255

Ser Thr Leu Ser Gln Glu Val Ser Asp Leu Val Glu Met Ile Trp Ala
            260                 265                 270
```

-continued

```
Glu Ala Leu Gly His Leu Glu His Met Leu Leu Lys Pro Val Asn Arg
                275                 280                 285

Ile Ser Leu Asn Asp Val Ser Lys Ala Glu Gly Ile Leu Leu Leu Val
            290                 295                 300

Lys Ala Leu Lys Asn Gly Glu Thr Ala Glu Gln Leu Gln Lys Met
305                 310                 315                 320

Met Thr Glu Phe Tyr Arg Leu Ile Pro His Lys Gly Thr Met Pro Lys
                    325                 330                 335

Glu Val Asn Leu Gly Leu Leu Ala Lys Lys Ala Asp Leu Cys Gln Leu
                340                 345                 350

Ile Arg Asp Met Val Asn Val Cys Glu Thr Asn Leu Ser Lys Pro Asn
                355                 360                 365

Pro Pro Ser Leu Ala Lys Tyr Arg Ala Leu Arg Cys Lys Ile Glu His
    370                 375                 380

Val Glu Gln Asn Thr Glu Glu Phe Leu Arg Val Arg Lys Glu Val Leu
385                 390                 395                 400

Gln Asn His His Ser Lys Ser Pro Val Asp Val Leu Gln Ile Phe Arg
                    405                 410                 415

Val Gly Arg Val Asn Glu Thr Thr Glu Phe Leu Ser Lys Leu Gly Asn
                420                 425                 430

Val Arg Pro Leu Leu His Gly Ser Pro Val Gln Asn Ile Val Gly Ile
                435                 440                 445

Leu Cys Arg Gly Leu Leu Leu Pro Lys Val Val Glu Asp Arg Gly Val
    450                 455                 460

Gln Arg Thr Asp Val Gly Asn Leu Gly Ser Gly Ile Tyr Phe Ser Asp
465                 470                 475                 480

Ser Leu Ser Thr Ser Ile Lys Tyr Ser His Pro Gly Glu Thr Asp Gly
                    485                 490                 495

Thr Arg Leu Leu Leu Ile Cys Asp Val Ala Leu Gly Lys Cys Met Asp
                500                 505                 510

Leu His Glu Lys Asp Phe Pro Leu Thr Glu Ala Pro Pro Gly Tyr Asp
                515                 520                 525

Ser Val His Gly Val Ser Gln Thr Ala Ser Val Thr Thr Asp Phe Glu
    530                 535                 540

Asp Asp Glu Phe Val Val Tyr Lys Thr Asn Gln Val Lys Met Lys Tyr
545                 550                 555                 560

Ile Ile Lys Phe Ser Met Pro Gly Asp Gln Ile Lys Asp Phe His Pro
                    565                 570                 575

Ser Asp His Thr Glu Leu Glu Glu Tyr Arg Pro Glu Phe Ser Asn Phe
                580                 585                 590

Ser Lys Val Glu Asp Tyr Gln Leu Pro Asp Ala Lys Thr Ser Ser Ser
                595                 600                 605

Thr Lys Ala Gly Leu Gln Asp Ala Ser Gly Asn Leu Val Pro Leu Glu
    610                 615                 620

Asp Val His Ile Lys Gly Arg Ile Ile Asp Thr Val Ala Gln Val Ile
625                 630                 635                 640

Val Phe Gln Thr Tyr Thr Asn Lys Ser His Val Pro Ile Glu Ala Lys
                    645                 650                 655

Tyr Ile Phe Pro Leu Asp Asp Lys Ala Ala Val Cys Gly Phe Glu Ala
                660                 665                 670

Phe Ile Asn Gly Lys His Ile Val Gly Glu Ile Lys Glu Lys Glu Glu
                675                 680                 685
```

```
Ala Gln Gln Glu Tyr Leu Glu Ala Val Thr Gln Gly His Gly Ala Tyr
    690                 695                 700

Leu Met Ser Gln Asp Ala Pro Asp Val Phe Thr Val Ser Val Gly Asn
705                 710                 715                 720

Leu Pro Pro Lys Ala Lys Val Leu Ile Lys Ile Thr Tyr Ile Thr Glu
                725                 730                 735

Leu Ser Ile Leu Gly Thr Val Gly Val Phe Phe Met Pro Ala Thr Val
            740                 745                 750

Ala Pro Trp Gln Gln Asp Lys Ala Leu Asn Glu Asn Leu Gln Asp Thr
        755                 760                 765

Val Glu Lys Ile Cys Ile Lys Glu Ile Gly Thr Lys Gln Ser Phe Ser
    770                 775                 780

Leu Thr Met Ser Ile Glu Met Pro Tyr Val Ile Glu Phe Ile Phe Ser
785                 790                 795                 800

Asp Thr His Glu Leu Lys Gln Lys Arg Thr Asp Cys Lys Ala Val Ile
                805                 810                 815

Ser Thr Met Glu Gly Ser Ser Leu Asp Ser Ser Gly Phe Ser Leu His
            820                 825                 830

Ile Gly Leu Ser Ala Ala Tyr Leu Pro Arg Met Trp Val Glu Lys His
        835                 840                 845

Pro Glu Lys Glu Ser Glu Ala Cys Met Leu Val Phe Gln Pro Asp Leu
    850                 855                 860

Asp Val Asp Leu Pro Asp Leu Ala Ser Glu Ser Glu Val Ile Ile Cys
865                 870                 875                 880

Leu Asp Cys Ser Ser Ser Met Glu Gly Val Thr Phe Leu Gln Ala Lys
                885                 890                 895

Gln Ile Thr Leu His Ala Leu Ser Leu Val Gly Glu Lys Gln Lys Val
            900                 905                 910

Asn Ile Ile Gln Phe Gly Thr Gly Tyr Lys Glu Leu Phe Ser Tyr Pro
        915                 920                 925

Lys His Ile Thr Ser Asn Thr Thr Ala Ala Glu Phe Ile Met Ser Ala
    930                 935                 940

Thr Pro Thr Met Gly Asn Thr Asp Phe Trp Lys Thr Leu Arg Tyr Leu
945                 950                 955                 960

Ser Leu Leu Tyr Pro Ala Arg Gly Ser Arg Asn Ile Leu Leu Val Ser
                965                 970                 975

Asp Gly His Leu Gln Asp Glu Ser Leu Thr Leu Gln Leu Val Lys Arg
            980                 985                 990

Ser Arg Pro His Thr Arg Leu Phe Ala Cys Gly Ile Gly Ser Thr Ala
        995                 1000                1005

Asn Arg His Val Leu Arg Ile Leu Ser Gln Cys Gly Ala Gly Val Phe
    1010                1015                1020

Glu Tyr Phe Asn Ala Lys Ser Lys His Ser Trp Arg Lys Gln Ile Glu
1025                1030                1035                1040

Asp Gln Met Thr Arg Leu Cys Ser Pro Ser Cys His Ser Val Ser Val
                1045                1050                1055

Lys Trp Gln Gln Leu Asn Pro Asp Ala Pro Glu Ala Leu Gln Ala Pro
            1060                1065                1070

Ala Gln Val Pro Ser Leu Phe Arg Asn Asp Arg Leu Leu Val Tyr Gly
        1075                1080                1085

Phe Ile Pro His Cys Thr Gln Ala Thr Leu Cys Ala Leu Ile Gln Glu
    1090                1095                1100

Lys Glu Phe Cys Thr Met Val Ser Thr Thr Glu Leu Gln Lys Thr Thr
```

-continued

```
1105                1110                1115                1120

Gly Thr Met Ile His Lys Leu Ala Ala Arg Ala Leu Ile Arg Asp Tyr
            1125                1130                1135

Glu Asp Gly Ile Leu His Glu Asn Glu Thr Ser His Glu Met Lys Lys
        1140                1145                1150

Gln Thr Leu Lys Ser Leu Ile Ile Lys Leu Ser Lys Glu Asn Ser Leu
    1155                1160                1165

Ile Thr Gln Phe Thr Ser Phe Val Ala Val Glu Lys Arg Asp Glu Asn
 1170                1175                1180

Glu Ser Pro Phe Pro Asp Ile Pro Lys Val Ser Glu Leu Ile Ala Lys
1185                1190                1195                1200

Glu Asp Val Asp Phe Leu Pro Tyr Met Ser Trp Gln Gly Glu Pro Gln
            1205                1210                1215

Glu Ala Val Arg Asn Gln Ser Leu Leu Ala Ser Ser Glu Trp Pro Glu
        1220                1225                1230

Leu Arg Leu Ser Lys Arg Lys His Arg Lys Ile Pro Phe Ser Lys Arg
    1235                1240                1245

Lys Met Glu Leu Ser Gln Pro Glu Val Ser Glu Asp Phe Glu Glu Asp
 1250                1255                1260

Gly Leu Gly Val Leu Pro Ala Phe Thr Ser Asn Leu Glu Arg Gly Gly
1265                1270                1275                1280

Val Glu Lys Leu Leu Asp Leu Ser Trp Thr Glu Ser Cys Lys Pro Thr
            1285                1290                1295

Ala Thr Glu Pro Leu Phe Lys Lys Val Ser Pro Trp Glu Thr Ser Thr
        1300                1305                1310

Ser Ser Phe Phe Pro Ile Leu Ala Pro Ala Val Gly Ser Tyr Leu Thr
    1315                1320                1325

Pro Thr Thr Arg Ala His Ser Pro Ala Ser Leu Ser Phe Ala Ser Tyr
 1330                1335                1340

Arg Gln Val Ala Ser Phe Gly Ser Ala Ala Pro Pro Arg Gln Phe Asp
1345                1350                1355                1360

Ala Ser Gln Phe Ser Gln Gly Pro Val Pro Gly Thr Cys Ala Asp Trp
            1365                1370                1375

Ile Pro Gln Ser Ala Ser Cys Pro Thr Gly Pro Pro Gln Asn Pro Pro
        1380                1385                1390

Ser Ala Pro Tyr Cys Gly Ile Val Phe Ser Gly Ser Ser Leu Ser Ser
    1395                1400                1405

Ala Gln Ser Ala Pro Leu Gln His Pro Gly Gly Phe Thr Thr Arg Pro
 1410                1415                1420

Ser Ala Gly Thr Phe Pro Glu Leu Asp Ser Pro Gln Leu His Phe Ser
1425                1430                1435                1440

Leu Pro Thr Asp Pro Asp Pro Ile Arg Gly Phe Gly Ser Tyr His Pro
            1445                1450                1455

Ser Ala Tyr Ser Pro Phe His Phe Gln Pro Ser Ala Ala Ser Leu Thr
        1460                1465                1470

Ala Asn Leu Arg Leu Pro Met Ala Ser Ala Leu Pro Glu Ala Leu Cys
    1475                1480                1485

Ser Gln Ser Arg Thr Thr Pro Val Asp Leu Cys Leu Leu Glu Glu Ser
 1490                1495                1500

Val Gly Ser Leu Glu Gly Ser Arg Cys Pro Val Phe Ala Phe Gln Ser
1505                1510                1515                1520

Ser Asp Thr Glu Ser Asp Glu Leu Ser Glu Val Leu Gln Asp Ser Cys
            1525                1530                1535
```

```
Phe Leu Gln Ile Lys Cys Asp Thr Lys Asp Asp Ser Ile Pro Cys Phe
            1540                1545                1550

Leu Glu Leu Lys Glu Glu Asp Glu Ile Val Cys Thr Gln His Trp Gln
        1555                1560                1565

Asp Ala Val Pro Trp Thr Glu Leu Leu Ser Leu Gln Thr Glu Asp Gly
    1570                1575                1580

Phe Trp Lys Leu Thr Pro Glu Leu Gly Leu Ile Leu Asn Leu Asn Thr
1585                1590                1595                1600

Asn Gly Leu His Ser Phe Leu Lys Gln Lys Gly Ile Gln Ser Leu Gly
            1605                1610                1615

Val Lys Gly Arg Glu Cys Leu Leu Asp Leu Ile Ala Thr Met Leu Val
            1620                1625                1630

Leu Gln Phe Ile Arg Thr Arg Leu Glu Lys Glu Gly Ile Val Phe Lys
        1635                1640                1645

Ser Leu Met Lys Met Asp Asp Pro Ser Ile Ser Arg Asn Ile Pro Trp
    1650                1655                1660

Ala Phe Glu Ala Ile Lys Gln Ala Ser Glu Trp Val Arg Arg Thr Glu
1665                1670                1675                1680

Gly Gln Tyr Pro Ser Ile Cys Pro Arg Leu Glu Leu Gly Asn Asp Trp
            1685                1690                1695

Asp Ser Ala Thr Lys Gln Leu Leu Gly Leu Gln Pro Ile Ser Thr Val
            1700                1705                1710

Ser Pro Leu His Arg Val Leu His Tyr Ser Gln Gly
        1715                1720
```